United States Patent
Narita et al.

(10) Patent No.: US 6,992,038 B2
(45) Date of Patent: Jan. 31, 2006

(54) ZINC CHLORIDE-LOADED SUPPORT AND METHOD FOR PRODUCING THE SAME

(75) Inventors: Mitsuo Narita, Niigata-ken (JP);
Masaki Tabata, Niigata-ken (JP);
Kazuhisa Hayakawa, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 87 days.

(21) Appl. No.: 10/714,954

(22) Filed: Nov. 18, 2003

(65) Prior Publication Data

US 2004/0138062 A1 Jul. 15, 2004

(30) Foreign Application Priority Data

Nov. 20, 2002 (JP) .................................... 2002-336122

(51) Int. Cl.
*B01J 27/06* (2006.01)
*B01J 21/18* (2006.01)
*B01J 27/138* (2006.01)
*C01B 9/00* (2006.01)
*C07C 17/00* (2006.01)

(52) U.S. Cl. ............... 502/224; 502/181; 502/183; 502/226; 502/237; 502/243; 502/253; 502/27; 502/34; 502/35; 502/55; 423/491; 423/622; 570/158; 570/258

(58) Field of Classification Search ............... 502/224, 502/226, 243, 253, 181, 183, 55, 237, 27, 502/34, 35; 423/622, 491, 594.14; 570/158, 570/258
See application file for complete search history.

(56) References Cited

U.S. PATENT DOCUMENTS

| | | | | |
|---|---|---|---|---|
| 1,743,740 A | * | 1/1930 | Von Girsewald et al. | ... 423/491 |
| 4,081,400 A | * | 3/1978 | Gorin | ........................... 502/37 |
| 4,136,056 A | * | 1/1979 | Zielke | ........................... 502/3 |
| 4,424,111 A | * | 1/1984 | Zielke et al. | ............... 208/419 |
| 4,490,534 A | | 12/1984 | Fujikawa et al. | |
| 4,810,797 A | | 3/1989 | Sharvit et al. | |
| 4,922,043 A | * | 5/1990 | Petrosky | ...................... 570/258 |
| 5,041,406 A | * | 8/1991 | Harley et al. | ............... 502/226 |
| 5,227,550 A | | 7/1993 | Shimizu et al. | |

FOREIGN PATENT DOCUMENTS

| | | |
|---|---|---|
| EP | 0 323 840 A1 | 7/1989 |
| EP | 0 501 501 A1 | 8/1992 |
| EP | 1421992 A1 * | 5/2004 |
| JP | 56-127324 A | 10/1981 |
| JP | 60115536 | 6/1985 |

* cited by examiner

*Primary Examiner*—J. A. Lorengo
*Assistant Examiner*—Patricia L. Hailey
(74) *Attorney, Agent, or Firm*—Foley & Lardner LLP

(57) ABSTRACT

The present invention is to solve the problems caused by a conventional method for producing a zinc chloride-loaded support wherein zinc chloride is adsorbed on a solid support in an aqueous solution of zinc chloride. The problems include environmental destruction caused by the treatment of a used aqueous solution of zinc chloride, corrosion to a reactor, a threat to health for workers, deterioration of zinc chloride due to deliquescence thereof, and reduction of specific surface area.

6 Claims, No Drawings

ZINC CHLORIDE-LOADED SUPPORT AND METHOD FOR PRODUCING THE SAME

BACKGROUND OF THE INVENTION

1. Field of the Invention

The present invention relates to a method for producing zinc chloride-loaded support wherein the zinc chloride is supported on a solid, and to the zinc chloride-loaded support. The zinc chloride-loaded support effectively acts, preferably as a catalyst, in a production of alkyl halide from alkyl alcohol or alkyl ether and hydrogen halide, in a chloroformyl reaction of hydrogen chloride and formaldehyde, in an olefine polymerization, or in a hydrocracking of heavy tar.

2. Description of the Related Art

Zinc chloride catalysts are used for a production of alkyl halide from alkyl alcohol or alkyl ether and hydrogen halide, for a chloroformyl reaction of hydrogen chloride and formaldehyde, and further, for an olefine polymerization and for a hydrocracking of heavy tar. In conventional methods, starting raw materials for these reactions are blown, in liquid or gas form, into an aqueous solution of zinc chloride catalyst at a temperature necessary for the reaction and at appropriate concentrations so as to contact the catalyst. Alternatively, the zinc chloride catalyst loaded on a solid support is used. For example, Japanese Patent Provisional Publication No. 56-127324 describes a method for producing methyl chloride comprising a step of bringing zinc chloride on activated carbon into contact with dimethyl ether and hydrogen chloride wherein the active carbon is used as a support. In order that zinc chloride is actually loaded on solid support such as activated carbon or solid material, one method comprises steps of dissolving solid zinc chloride so as to obtain an aqueous solution of zinc chloride at an ordinary temperature, impregnating the solid support such as activated carbon or solid material so that the aqueous solution of zinc chloride is adsorbed on the surface of or in porous portion of the solid support, removing the aqueous solution of zinc chloride which has not been adsorbed on the solid support, and optionally evaporating excessive water by heating so as to produce the support loading zinc chloride in an appropriate amount for a reaction on the surface thereof. Another method comprises spraying or adding dropwise an aqueous solution of zinc chloride to a solid support moving in a fluid bed or a rolling device so as to obtain the mixture and then optionally evaporating excessive water by heating so as to produce the support loading zinc chloride on the surface thereof.

SUMMARY OF THE INVENTION

A conventional method for supporting zinc chloride catalyst requires a preparation of an aqueous solution of zinc chloride which is strong in acidity and is toxic. In such a method, neutralization of the aqueous solution which has been used for the preparation of the catalyst is necessary before disposal, and an additional treatment of salt formed in the neutralization may also be necessary. The zinc chloride-loaded support which has adsorbed an aqueous solution of zinc chloride on the surface thereof may be optionally heated and then placed in a reaction tube where catalyst works. Alternatively, the unheated zinc chloride-loaded support may be placed in the reaction tube and then optionally heated to remove unnecessary water. This heating step sometimes has the problem of corrosion to the reaction tube since the aqueous solution of zinc chloride is strong in acidity and in corrosiveness.

Moreover, there is a threat to health for workers who have to handle toxic zinc chloride for storage during and after the catalyst preparation, for transfer, for an addition to a reactor and for others.

Further, since zinc chloride has a high deliquescence, it deteriorates during storage of zinc chloride before the catalyst preparation or storage of zinc chloride-containing catalyst after the preparation. There is a problem that the deterioration results in poor performance of catalyst. Therefore, such special care is required that the zinc chloride before the catalyst preparation and the zinc chloride-containing catalyst after the preparation should be stored in a sealed or dry room.

In addition, zinc chloride-loaded support prepared in a conventional method has an extremely reduced specific surface area. Thus, when the support contacts a gas or the like, a contact efficiency is low so that the result is unsatisfactory.

An object of the present invention is to solve the problems caused by the conventional method for producing zinc chloride-loaded support wherein zinc chloride is adsorbed on a solid support in an aqueous solution of zinc chloride. The problems include environmental destruction caused by the treatment of the used aqueous solution of zinc chloride, corrosion to the reactor, the threat to health for workers, the deterioration of zinc chloride due to deliquescence thereof, and reduction of specific surface area.

As a result of intensive investigations carried out in view of accomplishing the above object, the present inventors have found that zinc chloride-loaded support in which the zinc chloride is supported on the surface thereof can be prepared by mixing zinc oxide with a solid support beforehand so as to adsorb the zinc chloride on the surface of the solid support; introducing the resulting mixture into a reactor such as a reaction tube; blowing a hydrogen chloride gas, or water vapor containing gasified hydrogen chloride produced preferably by heating hydrochloric acid to boiling point thereof or higher, into the reactor, so as to convert the zinc oxide to zinc chloride in the reactor such as a reaction tube. The present invention has been completed on the basis of this finding.

The present invention provides a method for producing zinc chloride-loaded support in which the zinc chloride is supported on a solid support, comprising a step of bringing a mixture of a solid support and zinc oxide into contact with water vapor containing a hydrogen chloride gas or a hydrogen chloride gas so that the zinc oxide is chemically converted to zinc chloride. The present invention also provides a zinc chloride-loaded support produced by the above method.

Moreover, the present invention may preferably provide a method for producing alkyl halide comprising a step of reacting alkyl alcohol and/or alkyl ether with hydrogen halide, wherein the zinc chloride-loaded support is used as reaction catalyst.

According to the present invention, solid-supported catalyst of zinc chloride can be prepared without using an aqueous solution of zinc chloride which is toxic and strong in acidity. In addition, neutralization of a used aqueous solution after the preparation of the catalyst is unnecessary before disposal and a treatment of salt formed from the neutralization is also unnecessary.

Further, zinc chloride-loaded support can be prepared without handling the zinc chloride which is toxic and is easily deteriorating by deliquescence, for storage during and after the catalyst preparation, for transfer or for an addition of the catalyst to a reactor and for others. In contrast, handling of the zinc oxide is extremely easy since it has little toxicity to human bodies and does not deliquesce, and the prepared support has large specific surface area.

DETAILED DESCRIPTION OF THE PREFERRED INVENTIONS

A method for mixing zinc oxide and a solid support may include a method wherein support-particles and zinc oxide powder are mixed in a mixer such as a rolling-mixer; a method wherein support particles are dipped in a zinc chloride dispersion in which zinc oxide is dispersed in liquid such as water or organic solvent, filtered, and then optionally heated so as to evaporate excessive water or organic solvent; and a method wherein a zinc oxide dispersion in which zinc oxide is dispersed in liquid such as water or organic solvent is sprayed or added dropwise to a solid support which is being moved in a fluid bed or a rolling device, and then optionally heated so as to evaporate excessive water or organic solvent. Among these methods, unless there is a special reason, the method wherein support particles and zinc oxide powder are mixed may be more advantageous since a subsequent drying step can be omitted. In the method, a small amount of liquid such as water can be added for preventing the spattering of particles of zinc oxide or a support. This method can be carried out also in an inert gas such as a nitrogen gas.

The zinc oxide used in the present invention may be preferably in powder form. Although no particular limitation is placed on the particle size of zinc oxide powder, the average particle size may be 0.01 to 80 $\mu$m, particularly preferably 0.3 to 1.0 $\mu$m. When the zinc oxide has an average particle size smaller than 0.01 $\mu$m, the zinc oxide may have a high aggregation propensity. When the zinc oxide has an average particle size larger than 80 $\mu$m, the zinc chloride may have a poor adhesion, whereby zinc oxide particles may be difficult to be adsorbed on the surface of solid support when they are mixed with each other.

The solid support used in the present invention may be selected from solid supports which have good corrosion resistance to a highly acidic substance such as hydrogen chloride since the support is brought into contact with hydrogen chloride or a vapor component comprising hydrogen chloride. In addition, the solid support may be desirably heat resistant since it is frequently heated during reaction as a catalyst.

Preferable examples of the solid support may include activated carbon; oxide ceramics such as alumina, zirconia and magnesia; non-oxide ceramics such as silicon nitride and silicon carbide; and silica gel. Moreover, these supports may preferably have porous surface rather than flat surface so as to have a larger surface area.

The solid support are required to have a larger particle size than that of zinc oxide which will be mixed with the supports and may preferably have the average particle size of 0.1 to 20 mm or so in pellet form which may be in spherical or rice-bale shape.

The mixing ratio of the zinc oxide powder to the solid support may be appropriately selected so that the product will have preferable catalyst activity in a subsequent reaction. The ratio of bulk volume of the zinc oxide to that of the solid support may be preferably in the range of 5/95 to 70/30, wherein the bulk volume is the volume filled with particles.

The zinc oxide and the solid support has to be mixed at temperature under pressure in which the zinc oxide and the solid support do not deteriorate. It may be simple and easy that the zinc oxide and the solid support are mixed at room temperature under an atmosphere pressure.

A mixture of the zinc oxide and the solid support may be introduced into a reaction site, e.g., a reactor such as a reaction tube, in which the zinc oxide will be chemically converted to zinc chloride. The introduction can be done with a reserved funnel or a powder transfer device. The material of the reactor such as a reaction tube into which the mixture is introduced may be desirably corrosion-resistant to water vapor containing hydrogen chloride or a hydrogen chloride gas which will be introduced into the reactor such as a reaction tube after the introduction of the mixture. Specific examples of the material may include impermeable graphite materials, resin lining material, glass lining material, tantalum material, Hastelloy material, stainless material and carbon steel.

Chemical conversion of the zinc oxide into zinc chloride may be preferably done in a vessel in which the prepared zinc chloride-loaded support will be used. More specifically, it may be particularly preferable that the mixture of the zinc oxide and the solid support is introduced into a reactor in which the prepared zinc chloride-loaded support will be used, and then, the mixture is brought into contact with water vapor containing hydrogen chloride in the reactor so as to prepare zinc chloride-loaded support. This is because a reactor specialized for preparation of the zinc chloride-loaded support is not required and the transfer of the prepared zinc chloride-loaded support to a reactor in which the prepared zinc chloride-loaded support will be used is not required. Consequently, the transfer, storage or the other handlings of a toxic zinc chloride-loaded support or zinc chloride are not necessary and also the problem which deterioration of the zinc chloride by deliquescence during the transfer or storage thereof disappears.

The water vapor containing hydrogen chloride which will be flown into the reactor such as a reaction tube may be desirably prepared from an aqueous solution of hydrogen chloride wherein the concentration of hydrogen chloride may be 10 to 50% by weight, preferably 20 to 40% by weight. Even when a hydrogen chloride gas is used, the reaction proceeds since water is generated in-the reaction with zinc oxide. However, heat of formation of zinc chloride may be difficult to be removed. Thus, it may be preferable to use hydrogen chloride-containing water vapor which has been prepared from an aqueous solution of hydrogen chloride. An introduction temperature of the water vapor containing hydrogen chloride or the hydrogen chloride gas into the reactor in which the zinc chloride-loaded support has been placed may be preferably selected to be higher than the boiling point of an aqueous solution of hydrogen chloride as a reasonable temperature at which the reaction will take place smoothly and the reactor will not be corroded. The preferred temperature may be relatively 30 to 60° C. higher than the boiling point of an aqueous solution of hydrogen chloride and the particularly preferred temperature may be 105 to 200° C.

Moreover, a high introduction pressure of the water vapor containing hydrogen chloride or the hydrogen chloride gas into the reactor may not be preferred, since the boiling point of an aqueous solution of hydrogen chloride becomes higher due to the high introduction pressure so that the introduction temperature has to be set at a higher temperature.

When water vapor containing hydrogen chloride gas or hydrogen chloride gas is used, a diluent gas such as a nitrogen gas can be also used for preventing the increase in temperature. The concentration of the diluent gas, which is adjustable depending on a temperature, may be preferably adjusted so that the volume content of hydrogen chloride after the dilution becomes 2 to 100%.

The temperature of the reactor such as a reaction tube which the mixture of the zinc oxide and the solid support has been placed may be preferably set higher by some degrees than the temperature of water vapor containing a hydrogen chloride gas which will be introduced to the reactor so as to prevent condensation of hydrochloric acid. Specifically, the temperature may be preferably 170 to 250° C. When a hydrogen chloride gas is directly used, the temperature may be preferably 110 to 250° C. in view of prevention of increase in temperature.

The preferred amount of hydrogen chloride used for the reaction may be 1.0 to 1.2 times as much as the stoichometric amount for the chemical conversion of zinc oxide into zinc chloride in terms of mol.

When water vapor containing hydrogen chloride is being flowed into the reactor for the reaction, termination of the reaction can be confirmed by measuring a hydrogen ion concentration (pH) in the drop which has been generated by cooling the steam water coming out of the exit of the reactor. The termination point of the reaction, for example, may be the point where the pH having a value in the range of 5 to 7 falls down to the pH having 4 or less.

The reaction may be preferably carried out in a reactor which has been substituted with an inert gas such as a nitrogen gas. This is because oxidative deterioration of a burnable substance such as an active carbon in the present of oxygen at high temperature can be avoided. In addition, when water vapor containing hydrogen chloride or a hydrogen chloride gas is introduced into the reactor, an inert gas such as a nitrogen gas may be introduced at the same time.

Specific surface area of the zinc chloride-loaded support obtained by the method of the present invention becomes larger than that of conventional zinc chloride-loaded support obtained from an aqueous solution of zinc chloride.

The reason why the zinc chloride-loaded support of the present invention has a larger specific surface area is not certain. However, the following may be one of the reasons. According to the conventional method, an aqueous solution of zinc chloride allows the zinc chloride molecules penetrate into fine pores of a support, thereby causing blockage of inlets of the fine pores. In contrast, according to the present method, the zinc chloride molecules do not penetrate into the fine pores of the support since the solid form of zinc-oxide has been attached to the support.

The zinc chloride-loaded support of the present invention effectively acts, preferably as a catalyst, in a production of alkyl halide from alkyl alcohol and/or alkyl ether and hydrogen halide, in a chloroformyl reaction of hydrogen chloride and formaldehyde, in an olefine polymerization, or in a hydrocracking of heavy tar.

The zinc chloride-loaded support of the present invention can be useful preferably for the production of alkyl halide from alkyl alcohol and/or alkyl ether and hydrogen halide.

The alkyl alcohol may include methanol, ethanol, n-propanol and isoporpanol. Among them, preferred alcohol may be methanol.

The alkyl ether may include dimethyl ether, methyl ethyl ether and diethyl ether. Among them, preferred ether may be dimethyl ether.

The method for producing alkyl halide from alkyl alcohol and/or alkyl ether and hydrogen halide with zinc oxide catalyst may have a reaction condition similar to that of a conventional method. For example, preferable condition is as follows. The ratio of hydrogen halide to alkyl alcohol and/or alkyl ether may be 0.5 to 2.0 times as much as the stoichometric ratio in terms of mol. The reaction temperature may be in the range of 170 to 300° C., the reaction time may be in the range of 1 to 20 seconds and the reaction pressure may be in the gauge pressure range of 0 to 0.3 MPa. Since the zinc chloride-loaded support of the present invention has a larger specific surface area, the amount of catalyst can be reduced. This is one of the advantages of the present invention.

The present invention is more specifically explained with reference to the following examples and comparative examples. However, these examples are not to be construed to limit the scope of the invention.

EXAMPLE 1

The 100 kg of activated carbon (Trade name: Shirasagi, manufactured by Takeda Chemical Industries, Ltd.) having a diameter of approximately 4 mm and a length of approximately 6 mm, and 25 kg of first grade reagent of zinc oxide (manufactured by Kanto Kagaku Co.) having an average particle size of 0.6 $\mu$m were placed in a stainless steel cone-shaped mixer having a volume of 1 m$^3$, mixed at a rotation speed of 30 rpm for 5 minutes, and then discharged to obtain activated carbon-supported zinc oxide in which the zinc oxide has been mixed.

Provided were 15 carbon steel (STPG370-S) reaction tubes, each having an inner diameter of 54 mm, a thickness of 3.9 mm and a length of 5500 mm. The reaction tubes were placed in a vessel so that an oil as-heating medium can circulate around the tubes. The activated carbon-supported zinc oxide was placed in each of the reaction tubes and then left stand for 3 hours, keeping the heating medium at 180° C. so that the in-vessel temperature was 180° C.

After a nitrogen gas had been flowed into the reaction vessel at a rate of 15 m$^3$ per minute, water vapor containing hydrogen chloride was introduced into the reaction vessel at a rate of 17 kg per hour. The water vapor containing hydrogen chloride had been generated by heating a 20 wt % aqueous solution of hydrogen chloride in a carbon-made heater at a temperature of 180° C.

Hydrogen ion concentration (pH) in a drop generated by cooling steam water coming out of the outlet of the reaction vessel was measured. When the pH having 5 to 7 was down to 4 or less, this reaction was terminated. A small portion of the obtained product was taken out of the reactor and then its specific surface area was determined by using the BET method. The determined specific surface area was 367 m$^2$/g.

While the water vapor containing hydrogen chloride was continuously introduced into the reaction vessel at a rate of 65.1 kg per hour, keeping the heating medium of oil at 200° C., a dimethyl ether gas which had been heated to 180° C. was blown into the reaction vessel at a rate of 8.2 kg per hour. Then, the gas discharged out of the reaction vessel was analyzed with a gas chromatograph. Consequently, the gas found to be a gas composition wherein 95% of the dimethyl ether gas had been converted into methyl chloride was obtained. Thus, it is evident that the solid catalyst of the obtained zinc oxide-loaded support works as a catalyst for converting a dimethyl ether gas into methyl chloride.

COMPARATIVE EXAMPLE 1

The 90 kg of first grade reagent of zinc chloride (manufactured by Kanto Kagaku) was dissolved in 210 kg of pure water to obtain a aqueous 30 wt % solution of zinc chloride. The 100 kg of activated carbon (Trade name: Shirasagi, manufactured by Takeda Chemical Industries, Ltd.) having a diameter of approximately 4 mm and a length of approximately 6 mm was added to the above aqueous solution, left stand for 24 hours, filtered and dried at 100° C. to obtain a product. The specific surface area of the product was measured to be 150 m$^2$/g according to the BET method.

What is claimed is:

1. A method for producing a zinc chloride-loaded support in which zinc chloride is loaded on a solid support, comprising a step of bringing a mixture of the solid support and zinc oxide into contact with water vapor containing a hydrogen chloride gas or a hydrogen chloride gas so said zinc oxide is chemically converted into zinc chloride.

2. The method for producing a zinc chloride-loaded support according to claim 1, wherein said zinc oxide is in powder form.

3. The method for producing a zinc chloride-loaded support according to claim 1, wherein said chemical conversion of zinc oxide into zinc chloride is done in a vessel in which said zinc chloride-loaded support will be used.

4. The method for producing a zinc chloride-loaded support according to claim 2, wherein said chemical conversion of zinc oxide into zinc chloride is done in a vessel in which said zinc chloride-loaded support will be used.

5. The method for producing a zinc chloride-loaded support according to claim 1, wherein said solid support is selected from the group consisting of activated carbon, ceramic and silica gel.

6. The method for producing a zinc chloride-loaded support according to claim 2, wherein said solid support is selected from the group consisting of activated carbon, ceramic and silica gel.

* * * * *